(12) United States Patent
Bodermann

(10) Patent No.: US 7,420,689 B2
(45) Date of Patent: Sep. 2, 2008

(54) METHOD FOR DETERMINING THE REFRACTIVE INDEX DURING INTERFEROMETRIC LENGTH MEASUREMENT AND INTERFEROMETRIC ARRANGEMENT THEREFOR

(75) Inventor: Bernd Bodermann, Braunschweig (DE)

(73) Assignee: Bundesrepublik Deutschland, vertr. durch das Bundesministerium fur Wirtschaft und Technologie, dieses vertreten durch den Prasidenten der Physikalisch-Technischen Bundesanstalt, Braunschweig (DE)

( * ) Notice: Subject to any disclaimer, the term of this patent is extended or adjusted under 35 U.S.C. 154(b) by 239 days.

(21) Appl. No.: 10/564,449

(22) PCT Filed: Jun. 24, 2004

(86) PCT No.: PCT/DE2004/001321

§ 371 (c)(1),
(2), (4) Date: Jul. 26, 2006

(87) PCT Pub. No.: WO2005/015122

PCT Pub. Date: Feb. 17, 2005

(65) Prior Publication Data

US 2007/0024859 A1    Feb. 1, 2007

(30) Foreign Application Priority Data

Jul. 25, 2003   (DE) ................... 103 34 350

(51) Int. Cl.
*G01B 11/02* (2006.01)
*G01B 9/02* (2006.01)

(52) U.S. Cl. ...................... 356/517; 356/486

(58) Field of Classification Search ........... 356/481, 356/482, 486, 487, 492, 498, 500, 517
See application file for complete search history.

(56) References Cited

U.S. PATENT DOCUMENTS 3,877,813 A    4/1975    Hayes et al.

(Continued)

FOREIGN PATENT DOCUMENTS

DE    19727402    2/1998

(Continued)

OTHER PUBLICATIONS

G. Bonsch et al., "Measurement of the Refractive Index of Air and Comparison with Modified Edlen's Formulae"; Metrologia, 1998 vol. 35, pp. 133-139.

(Continued)

*Primary Examiner*—Patrick J Connolly
(74) *Attorney, Agent, or Firm*—Whitham, Curtis, Christofferson & Cook, PC

(57) ABSTRACT

The aim of the invention is to determine the refractive index and/or compensation of the influence of the refractive index during interferometric length measurement with the aid of an interferometer (13, 13') impinged upon by at least two measuring beams ($v_2$, $v_3$) having at least defined frequencies with an approximately harmonic ratio. Interferometric phases are evaluated for the at least two measuring beams ($v_2$, $v_3$) at the outlet of said interferometer. The interferometric phases corresponding to the harmonic ratio of the frequencies of the measuring beams ($v_2$, $v_3$) are multiplicated and at least one phase difference of the thus formed phase value is examined. According to the invention, at least one of the measuring beams ($v_3$) can be modified in the frequency thereof and a control signal which is used to modify the frequency of the measuring beam ($v_3$) which can be modified in the frequency thereof is formed from the obtained phase difference and the measuring signal controls the frequency in such a manner that the phase difference in zero. It is also possible to determine the refractive index or the length measurement by measuring a frequency difference.

9 Claims, 3 Drawing Sheets

U.S. PATENT DOCUMENTS

Figure 1:
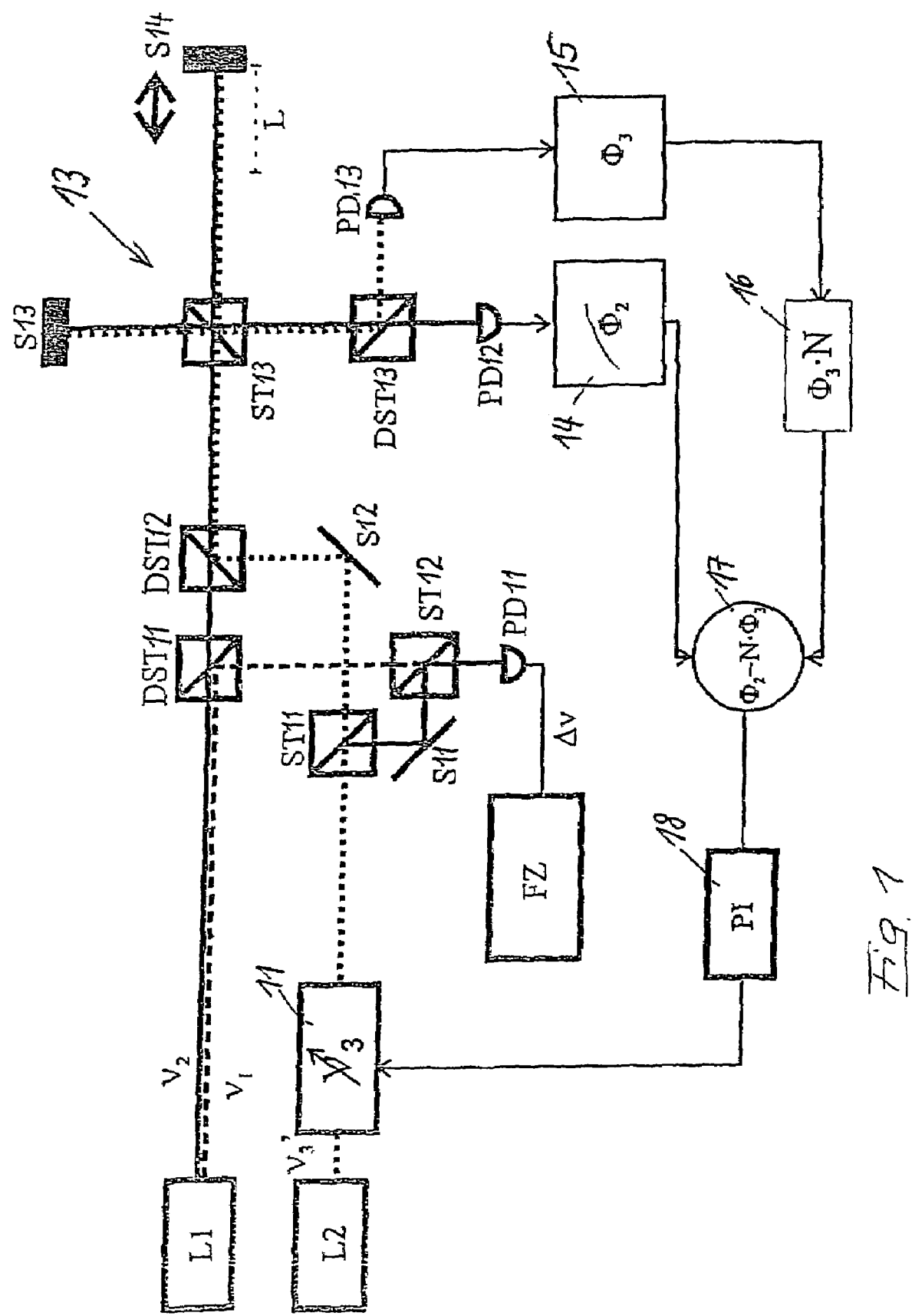

| | | |
|---|---|---|
| 4,948,254 A | 8/1990 | Ishida |
| 5,404,222 A | 4/1995 | Lis |
| 5,412,474 A | 5/1995 | Reasenberg et al. |
| 5,537,209 A | 7/1996 | Lis |
| 5,764,362 A | 6/1998 | Hill et al. |
| 5,838,485 A | 11/1998 | de Groot et al. |
| 6,014,216 A | 1/2000 | Zorabedian |
| 6,219,144 B1 | 4/2001 | Hill et al. |
| 6,327,039 B1 | 12/2001 | de Groot et al. |
| 6,417,927 B2 | 7/2002 | de Groot |
| 2002/0001086 A1* | 1/2002 | De Groot ............... 356/486 |
| 2002/0131053 A1* | 9/2002 | Groot et al. ............. 356/517 |
| 2002/0140945 A1* | 10/2002 | de Groot et al. ......... 356/517 |
| 2002/0140946 A1* | 10/2002 | Groot et al. ............. 356/517 |

FOREIGN PATENT DOCUMENTS

| | | |
|---|---|---|
| DE | 19727404 | 2/1998 |
| GB | 2346967 | 8/2000 |
| WO | WO99/42787 | 8/1999 |

OTHER PUBLICATIONS

B. Boermann et al., "Improved Second Harmonic Two Wavelength Interferometer with Refractive Index Correction without Effect Modulation"; Proc. of SPIE, vol. 5190, 2003; pp. 339-346.

* cited by examiner

METHOD FOR DETERMINING THE REFRACTIVE INDEX DURING INTERFEROMETRIC LENGTH MEASUREMENT AND INTERFEROMETRIC ARRANGEMENT THEREFOR

The invention relates to a method for determining the refractive index and/or compensation of the influence of refractive index during interferometric length measurements with the aid of an interferometer to which there are applied at least two measuring beams having at least defined frequencies approximately at a harmonic ratio to one another, and at whose output phases for the at least two measuring beams are evaluated, the interferometric phases being multiplied in an interferometrically fashion corresponding to the harmonic ratio of the frequencies of the measuring beams and at least one phase difference of the phase values thus formed being examined.

The invention also relates to an interferometer arrangement for carrying out the method having at least one coherent radiation source for generating at least two measuring beams having defined frequencies approximately at a harmonic ratio to one another and having an interferometer whose output signals are passed to a beam splitter separating the measuring beams, the separated measuring beams being passed to optoelectronic transducers, and at least one of the output signals of the optoelectric transducers being fed to a multiplier corresponding to the harmonic ratio of the frequencies of the measuring beams.

It is known to use an interferometer to carry out distance measurements and/or measurements of changes in physical lengths. In the case of such a measurement, the optical path length is measured that is composed of the physical path length and the integral refractive index of the medium on the measured path length. The influence of the refractive index on the measurement can be eliminated by virtue of the fact that the interferometric measurement is carried out with two defined different wavelengths. Since the refractive index depends on the wavelength, while the physical path length is independent of the wavelength, it is thereby possible for items of information relating to the physical path length and refractive index to be separated from one another.

U.S. Pat. No. 4,948,254 describes an apparatus that operates using this dispersion method. The two wavelengths are supplied by an argon ion laser in combination with a frequency doubler crystal. Two waves that are basically phase-locked are produced for the interferometry by using a fundamental wave and a frequency-doubled wave. The doubler crystal is located at the start of the measuring distance at the measuring arm of a two-beam interferometer. The outgoing fundamental wave produces a colinearly running harmonic in the crystal. Both waves traverse the measuring distance. Upon returning through the crystal, the fundamental wave produces a second harmonic, which has a phase difference with respect to the first harmonic because of the dispersion in the medium being traversed. This phase difference, which is to be measured, constitutes the measuring signal. It is a measure of the dispersion and thus of the refractive indices. The phase difference is dependent only slightly on other influences such as the position and state of movement of the interferometer, and so the phase difference constitutes a useful measuring signal for an accurate measurement. However, there is the problem that determining the phases accurately is complicated and saddled with fundamental measurement uncertainties.

U.S. Pat. No. 5,404,222 describes a similar system, in which the double crystal is traversed before the light used enters the interferometer. Moreover, frequency doubling takes place at the output of the interferometer.

A so-called superheterodyne interferometer is known from U.S. Pat. No. 5,838,485, for example, for the purpose of improving the measuring accuracy. Here, as well, a two-wavelength interferometer with harmonically corrected optical waves is used in order to compensate the influence of the refractive index by means of the dispersion method. With the superheterodyne interferometer, the interferometric phases of the optical fundamental wave and harmonic are respectively mapped onto high-frequency heterodyne frequencies. The interferometric phase of the heterodyne signal of the fundamental wave is doubled. The difference between this doubled phase and the phase of the heterodyne signal of the harmonic is proportional to the dispersion. The advantage of the superheterodyne interferometer consists in that the sensitivity of the compensation of the refractive index with reference to the mechanical stability of the interferometer is much lower. However, the accuracy of measurement that can be achieved is limited by the determination of the phase difference. For the high frequency signals, the phase measurements must be performed more accurately by 1 to 2 orders of magnitude, than for the actual length measurement. The measurement of two independent phases is required in order to determine the phase difference. Possible nonlinearities in the phase measurement influence the measurement uncertainty. The differential phase changes periodically with the measuring distance and so the determination of the refractive index is not unique. Furthermore, the measuring distance must be changed in order to determine the refractive index. The method is therefore suitable only for displacement measurements accompanied by refractive index compensation, but not for position measurements accompanied by refractive index compensation, for example in an interferometer with absolute measurement.

Furthermore, US 2002/0001086 A1 discloses combining a two-wavelength interferometer with a refractometer that is placed in the vicinity of the distance to be measured interferometrically. The refractometer, which comprises a balanced interferometer of fixed path lengths, the reference distance running in vacuum and the measuring distance running in the ambient air, serves the purpose of measuring the long term changes in the refractive index, and can be used to determine the inverse dispersion A when the composition of the air is changing. The refractive index can be determined uniquely and in absolute terms given this supplement.

It is the object of the present invention to improve a method and apparatus of the type mentioned at the beginning such that the influences of refractive index can be more accurately compensated for precision length measurements.

According to the invention, in order to achieve this object the method of the type mentioned at the beginning is characterized in that at least one of the measuring beams is of variable frequency, and in that from the phase difference formed a control signal is formed in order to vary the frequency of the variable frequency measuring beam and is used to control the frequency such that the phase difference vanishes.

Furthermore, according to the invention in order to achieve the object an apparatus of the type mentioned at the beginning is characterized in that the frequency of at least one of the measuring beams can be varied by means of a frequency controller, and in that a phase comparator for the phases of the output signals of the optoelectronic transducers, is used to generate a control signal representing a phase difference, which control signal is fed to the frequency controller to form a control loop for the interferometric phases.

According to the invention, an interferometric phase-locked loop is implemented which ensures that the integral optical wavelengths of the two beams circulating in the interferometer are exactly harmonically correlated along the measuring distance. The correlation corresponds to the harmonic frequency ratio of the fields of the two-frequency radiation source. For this purpose, the frequency of one of the measuring beams is adjusted by a certain frequency amount, the offset frequency. The differential frequency between the exactly harmonic frequency ratio and the frequency set by the control loop is a direct measure of the integral refractive index on the measuring distance. The offset frequency can be measured easily, and is, in particular, independent of the length of the measuring distance and of mechanical instabilities of the interferometer. Since, according to the invention, the measurement of the refractive index can be reduced to a frequency measurement, a higher measuring accuracy is achieved in principle, given that frequencies are physical quantities that can be measured very accurately. Furthermore, by contrast with the measurement of a periodic phase, the frequency measurement is a priori unique and measurement can be carried out in principle without effect modulation.

The measurement of the offset frequency is preferably performed by virtue of the fact that at least one reference beam is generated at a frequency that corresponds approximately to the frequency of one of the measuring beams and is coupled to the frequency of another measuring beam, and in that a frequency difference is measured between the frequency of the reference beam and the frequency of the corresponding measuring beam.

The method according to the invention and the interferometer arrangement according to the invention can be modified by applying the superheterodyne principle. In particular, it is possible in this case for high frequencies that are at the same harmonic ratio to one another as the frequencies of the measuring beams to be modulated onto the superimposed measuring beams in a reference branch of the interferometer.

It is also possible in a further modification of the present invention to make use of different polarization components, one polarization component being displaced from the other by $\pi/2$ by means of a $\lambda$ retardation plate. It is thereby achieved that there are always available for accurate evaluation signal components that are not zero and can therefore be effectively measured.

Figure 2:
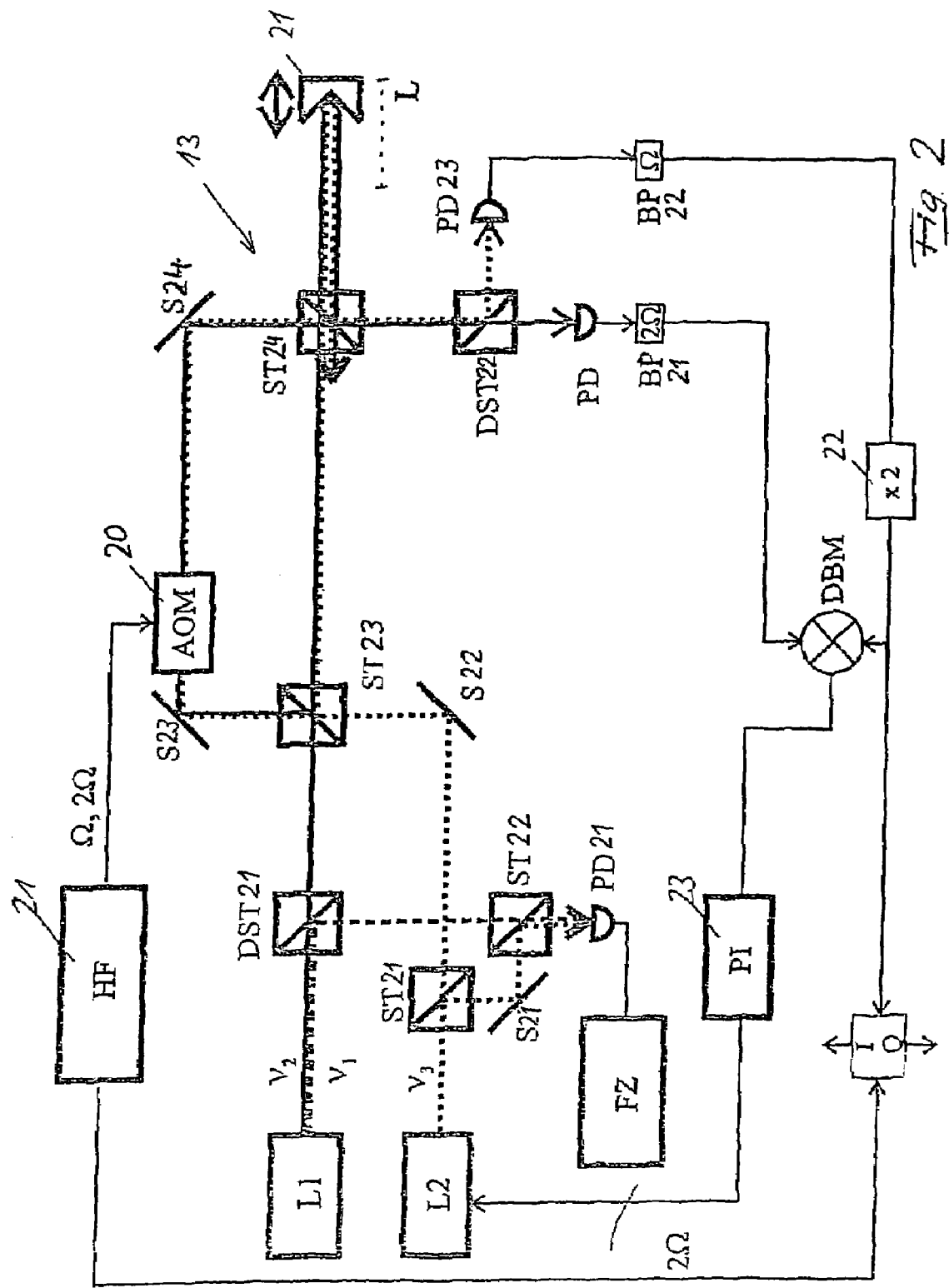
Figure 3:
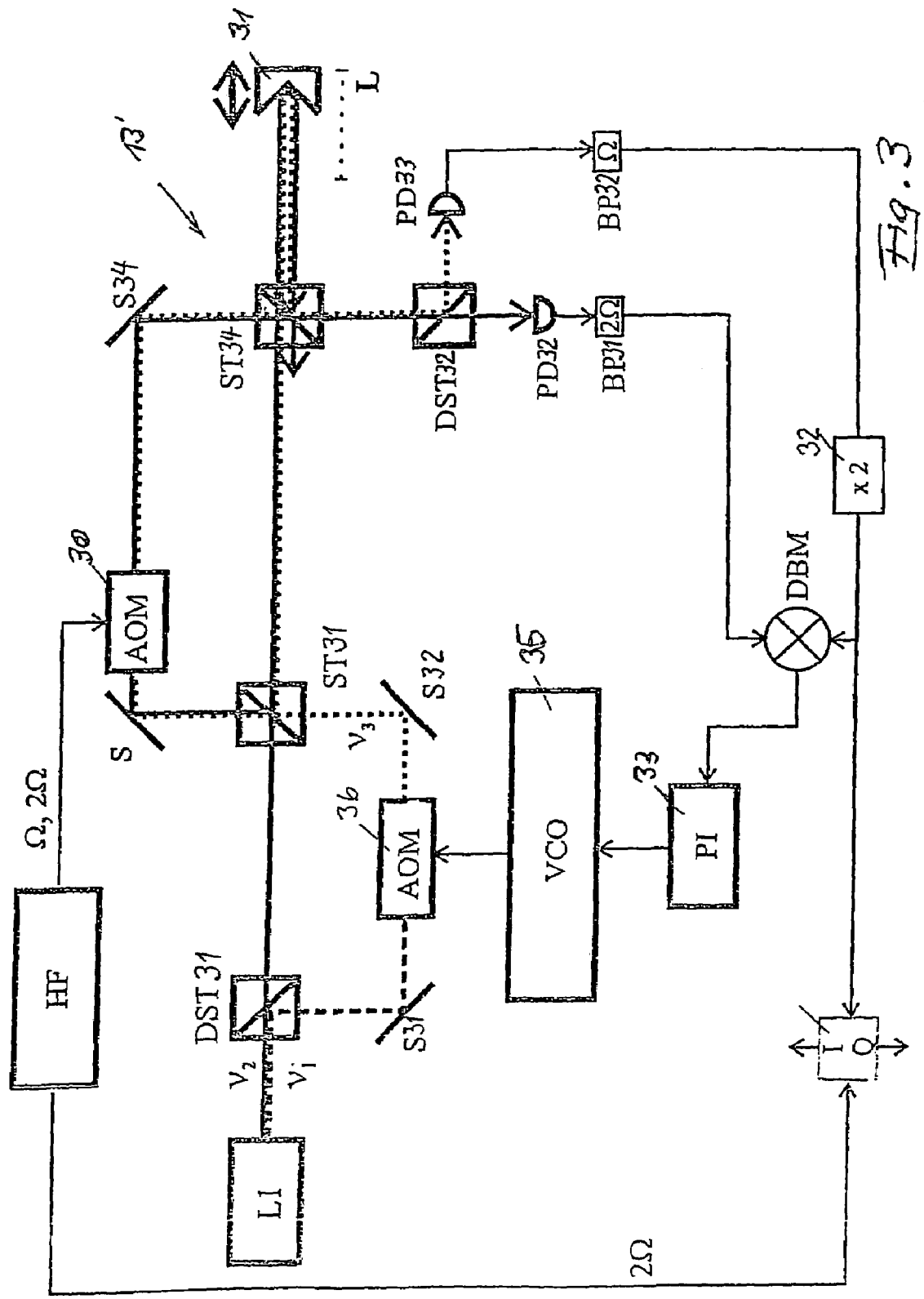

The invention is to be explained in more detail below with the aid of exemplary embodiments illustrated in the drawing, in which:

FIG. 1 shows a schematic of an interferometer arrangement according to the invention, FIG. 2 shows a schematic of an embodiment of the interferometer arrangement according to the invention, as a superheterodyne interferometer with two laser sources, FIG. 3 shows a variant of the embodiment in accordance with FIG. 2, with a single laser source.

Provided in the embodiment in accordance with FIG. 1 as coherent radiation source is a laser L1 that emits a laser beam at frequency $v_1$, as reference beam, and at a second frequency $v_2$ as first measuring beam. The laser L1 can be, for example, a second harmonic generator (SHG) laser that also emits a frequency-doubled field $v_2=2v_1$ in addition to its fundamental frequency $v_1$. However, the application of the invention is not limited to frequency doubling. What is essential is a harmonic correlation of the frequencies in the general form of $k1 \cdot v_1 = k2 \cdot v_2$, $k1$, $k2$ being natural numbers. In a preferred form that is easy to implement, it holds that $v_2 = N \cdot v_1$ (N being a natural number >1).

A second laser source L2 emits a laser beam at a third frequency $v_3$ that corresponds to the frequency $v_1$.

In the exemplary embodiment illustrated, the output frequency of the laser L2 can be controlled by a frequency controller 11. The frequency controller can be an acousto-optic modulator (AOM), but also a frequency control input of a laser L2 of tunable frequency.

The output beam of the laser L1 passes to a dichroic beam splitter DST 11 that deflects the beam of the laser L1 at frequency $v_1$ as reference beam, and passes the beam at frequency $v_2$ as first measuring beam. The first measuring beam $v_2$ traverses a second dichroic beam splitter DST12 and passes into an interferometer 13.

The frequency $v_3$, of the second laser L2 is influenced by the frequency controller 11 and, as frequency $v_3$, emerges as second measuring beam from the frequency controller 11. It is split by a neutral beam splitter ST11 into two components of which one is deflected out of the beam path and guided onto a mirror ST11, the partial beam passing to a further neutral beam splitter ST12, as a result of which the deflected component of the second measuring beam $v_3$ is superimposed collinearly on the reference beam deflected by the dichroic beam splitter DST11. The superimposed measuring beam passes to a photodetector PD11. If the frequencies $v_3$ and $v_1$ correspond, a differential frequency $\Delta v = \phi$ is produced. However, if a frequency deviation is present, an oscillation frequency $\Delta v = |v_1 - v_3|$ is measured with the aid of a frequency counter FZ.

The portion of radiation for the second measuring beam $v_3$ that is transmitted through the beam splitter ST11 is collinearly superimposed on the first measuring beam $v_2$ via a mirror S12 and the dichroic beam splitter DST12, and so both measuring beams $v_2$, $v_3$ pass to a beam splitter ST13 of the interferometer 13. The neutral beam splitter ST13 splits the incoming measuring beam (formed from the superimposed measuring beams $v_1$, $v_2$) into a reference arm guided to the reference mirror S13 and into a measuring arm of the interferometer 13, which is formed by a measuring mirror S14. The beams reflected by the reference mirror ST13 and by the measuring mirror S14 are superimposed by the beam splitter DST13 and pass to a dichroic beam splitter DST13 at the output of the interferometer 13. The dichroic beam splitter DST13 separates the two frequencies $v_1$, $v_3$ from one another, since the frequency $v_3$ is deflected by the dichroic beam splitter DST13 onto the photodetector PD13 while the frequency $v_2$ of the first measuring beam traverses the dichroic beam splitter DST13 and passes to a photodetector PD12.

The phases $\phi2$ and $\phi3$ produced by the measuring beams $v_2$, $v_3$ are separated by means of one of the known methods for detecting the interferometric phase, this being done with the aid of suitable evaluation electronics 14, 15, and processed.

For the phases, it holds that $$\phi 2 = \frac{4\pi \cdot L \cdot n_2 \cdot v_2}{c} \text{ and}$$

$$\phi 3 = \frac{4\pi \cdot L \cdot n_3 \cdot v_3}{c},$$

$n_2$, $n_3$ being the integral refractive index along the distance L for the optical frequency $v_2$ and $v_3$, respectively, and c being the speed of light (in vacuum).

Since the frequencies $v_2$ and $v_3'$ are harmonically correlated to $v_2 = N \cdot v_3'$, and the frequency control range of the frequency controller 11 effects only small changes in frequency, as will be explained in yet more detail, it holds that $v_2 \approx N \cdot v_3'$.

It can also hold that $$\phi_2 \approx N \cdot \phi_3.$$

The interferometric phase $\phi_3$ is not multiplied in a multiplying stage 16 by the factor N, and the phase thus formed is compared with the phase $\phi_2$ in a phase comparator 17 by forming the difference $$\Delta\phi = \phi_2 - N \cdot \phi_3$$

This differential signal is amplified via a control amplifier 18 that is a PI amplifier (Proportional Integral Amplifier) in the exemplary embodiment illustrated, and is fed to the frequency control stage 11 such that $$\Delta\phi = \phi$$

holds as control criterion. The result is the implementation of an interferometric phase-locked loop that ensures that the integral optical wavelengths of the two beams circulating in the interferometer are exactly harmonically correlated along the measuring distance L of the interferometer 13 in accordance with $$N \cdot \lambda_2 = \lambda_3, \quad \lambda_2 = \frac{c}{v_2 \cdot n_2}, \quad \lambda_3 = \frac{c}{v_3 \cdot n_3}.$$

It is thereby possible to calculate the integral refractive index n2 from $$n_2 = \frac{v_2 + N \cdot \Delta v}{v_2 + N \cdot \Delta v - N \cdot A \cdot \Delta v}$$

from the knowledge of the optical frequency $v_2$ and the measurement of the frequency difference $\Delta v$ in the frequency counter FZ. The inverse dispersion A that is included in this expression and defined as $$A = \frac{n_2 - 1}{n_2 - n_3}$$

can be calculated for measuring distances in air of normal composition from the so-called modified Edlen formula (compare G. Bönsch, E. Potulski "Measurement of the refractive index of air and comparison with modified Edlen's formulae", Metrologia 35 (1998), 133-139), or can be measured with the aid of a suitable apparatus (compare US 2002/0001086 A1).

The physical path length difference L in the interferometer is therefore yielded as $$L = \frac{\phi_2 \cdot c}{4\pi \cdot n_2 \cdot v_3}$$
$$= \frac{\phi_2 \cdot c}{4\pi \cdot \frac{v_2 + N \cdot \Delta v}{v_2 + N \cdot \Delta v - N \cdot A \cdot \Delta v} \cdot v_2}$$
$$= \frac{c \cdot \phi_2 \cdot (v_2 + N \cdot \Delta v - N \cdot A \cdot \Delta v)}{4 \cdot \pi \cdot v_2 \cdot (v_2 + N \cdot \Delta v)}$$

Given a displacement measurement of the measuring mirror S14 or a position measurement, it is therefore possible with the aid of the invention for both the refractive index and the refractive index fluctuations to be compensated with high precision along the distance to be measured. In the case of the exemplary embodiment illustrated in FIG. 2, the first laser L1 emits the frequencies $v_1$, $v_2$, while the second laser L2 is designed as a laser of tunable frequency and therefore emits the frequency $v_3$. As in FIG. 1—the dichroic beam splitter DST21, the neutral beam splitters ST21 and ST22 and the mirror S21 are provided for measuring the frequency difference $\Delta v = |v_3 - v_1|$. The optical frequency difference is converted electrically by the photodetector 21 and evaluated electrically in the frequency counter FZ. The second measuring beam $v_3$ is not superimposed until in the measuring beam $v_2$ via the mirror S22 and the beam splitter ST23, and is guided in this form to the interferometer 13'. However, the superimposed beams are also guided via a mirror S23 onto an acoustooptic modulator (AOM) 20 that shifts the frequency of at least portions of the two beams. As a result, the frequency of the beam at optical frequency $v_2$ is shifted by the (radio) frequency $2\Omega$, and the frequency of the beam at optical frequency $v_3$ is shifted by the frequency $\Omega$. For this purpose, the frequencies $\Omega$, $2\Omega$ are led via a high frequency generator 21 to a control input of the AOM 20. The two optical beams traverse the AOM collinearly. Since, in accordance with the exemplary embodiment illustrated, the optical frequencies $v_3$ and $v_2$ form to a very good approximation the same frequency ratio as the high frequencies $\Omega$ and $2\Omega$, the Bragg condition in AOM is, as further explained below, simultaneously filtered electronically and optically in one spatial direction for the optical frequency $v_3$ and the high frequency $\Omega$, and therefore does not disturb the measurement method described here.

The two partial beams collinearly superimposed in the beam splitter ST23 and guided directly into the interferometer 13' pass through the beam splitter ST24 and are reflected at a reflector 21, which can be displaced within the measuring path length L, and guided through the beam splitter 24 onto a dichroic beam splitter 22. The reflector 21 is designed as a silvered roof prism in the exemplary embodiment illustrated. The reflected measuring beams are collinearly superimposed at the output of the beam splitter 24 with the reference beams modulated by the AOM 20. The dichroic beam splitter DST 22 separates the beams into two partial beams that are converted into electric signals by means of photodetectors PD23 and PD24. The component passing through the dichroic beam splitter DST22 has a beat at the frequency $2\Omega$. This is extracted from the electric signal at the frequency $2\Omega$ by means of a suitable bandpass filter BP21. Similarly, the beams reflected at the dichroic beam splitter DST22 generate at the detector PD23 a beat signal of frequency $\Omega$ that is once again extracted from the detector signal by means of a suitable bandpass filter BP22 of frequency $\Omega$.

With this heterodyne interferometer, the interferometric phase shift, produced by a displacement of the reflector 21, between reference beam and measuring beam is mapped onto an equally large phase shift of the heterodyne frequency. Since it holds that $v_2$ is approximately $2 \cdot v_3$, and that it also holds for the optical wavelengths that $\lambda_3 \approx 2 \cdot \lambda_2$, given a displacement of the reflector 21 the resulting phase shift of the heterodyne signal of frequency $2\Omega$ is approximately twice as large in the double heterodyne interferometer described here than the resulting phase shift in the heterodyne signal of frequency $\Omega$. The latter phase shift is doubled with the aid of a high frequency frequency doubler 22, and the phase of the doubled signal is compared with the phase of the heterodyne signal of frequency $2\Omega$ with the aid of a phase comparator DBM in the form of a doubly balanced mixer. The phase comparator includes a downstream low pass filter with a suitable cutoff frequency $<< 4\Omega$.

With the aid of a PI controller 23, the frequency of the beam v3 emitted by the laser L2 is varied until the output signal of the phase comparator DBM vanishes and so it holds for the optical wavelengths that $\lambda_3=2\lambda_2$. A small path length difference $\Delta L$ of the measuring length L of the interferometer 13' can be set for the purpose of producing the uniqueness of the control, which is not inherently ensured by the periodic output signal of DBM. The path length difference $\Delta L$ must thus be prescribed so that for the ambiguous output signal DBM a larger frequency difference $\Delta v$ to be set as maximum differential frequency $\Delta v_{max}$. Control is uniquely possible in this case with only one $\Delta v$.

An interferometric phase-locked loop which ensures that $\lambda_3=2\cdot\lambda_2$ holds is thus implemented again. It holds that:

$$n_2 = \frac{v_2 + 2\cdot\Delta v}{v_2 + 2\cdot\Delta v - 2\cdot A\cdot\Delta v}$$

and that $$L = \frac{c\cdot\phi_2\cdot(v_2 + 2\cdot\Delta v - 2\cdot A\cdot\Delta v)}{2\cdot\pi\cdot v_2\cdot(v_2 + 2\cdot\Delta v)}$$

for the physical path length difference L in the interferometer. The phase $\phi_2$ required therefor can be obtained by means of known techniques, for example by means of a commercially available I/Q demodulator 24.

A possible modification of the design of the invention in accordance with FIG. 2 that manages with only one laser L1 is illustrated in FIG. 3. The beam of frequency $v_1$ emitted by the laser L1 is frequency shifted by the frequency $\Delta v$ by means of a very wide band, for example acoustooptic frequency shifter AOM 36, such that $v_3=v_1+\Delta v$.

Such wide band frequency shifters with a voltage controlled microwave driver (VCO) 35 are commercially available. Otherwise, the exemplary embodiment corresponds substantially to FIG. 2, the measure of the frequency difference that serves as measuring signal resulting directly from the frequency for the VCO 35.

The invention claimed is:

1. A method for determining the refractive index and/or compensation of the influence of refractive index during interferometric length measurements with the aid of an interferometer (13, 13') to which there are applied at least two measuring beams ($v_2$, $v_3$) having at least defined frequencies approximately at a harmonic ratio to one another, and at whose output phases for the at least two measuring beams ($v_2$, $v_3$) are evaluated, the interferometric phases being multiplied in an interferometrically fashion corresponding to the harmonic ratio of the frequencies of the measuring beams ($v_2$, $v_3$) and at least one phase difference of the phase values thus formed being examined, characterized in that at least one of the measuring beams ($v_3$) is of variable frequency, and in that from the phase difference formed a control signal is formed in order to vary the frequency of the variable frequency measuring beam ($v_3$) and is used to control the frequency such that the phase difference vanishes.

2. The method as claimed in claim 1, characterised in that at least one reference beam ($v_1$) is generated at a frequency that corresponds approximately to the frequency of one of the measuring beams ($v_3$) and is coupled to the frequency of another measuring beam ($v_2$), and in that a frequency difference is measured between the frequency of the reference beam ($v_1$) and the frequency of the corresponding measuring beam ($v_3$).

3. The method as claimed in claim 2, characterized in that one of the measuring beams ($v_2$) and the reference beam ($v_1$) are generated by a coherent radiation source (L1) with a frequency multiplier.

4. The method as claimed in claim 1, characterized in that the two measuring beams ($v_2$, $v_3$) are derived from a beam of a coherent radiation source (L1) by means of a frequency splitter (36).

5. The method as claimed in claim 1, characterized in that high frequencies ($\Omega$, $2\Omega$) that are at the same harmonic ratio to one another as the frequencies of one of the measuring beams ($v_2$) to the reference beam ($v_1$) are modulated onto the superimposed measuring beams ($v_2$, $v_3$) in a reference branch of the interferometer (13').

6. An interferometer arrangement for carrying out the method as claimed in claim 1, having at least one coherent radiation source (L1, L2) for generating at least two measuring beams ($v_2$, $v_3$) having defined frequencies approximately at a harmonic ratio to one another and having an interferometer (13, 13') whose output signals are passed to a beam splitter (DST 13, DST 22, DST 32,) separating the measuring beams, the separated measuring beams being passed to optoelectronic transducers (PD12, PD13; PD22, PD23; PD32, PD33), and at least one of the output signals the optoelectric transducers being fed to a multiplier (16, 22, 32) corresponding to the harmonic ratio of the frequencies of the measuring beams ($v_2$, $v_3$), characterized in that the frequency of at least one of the measuring beams (v3) can be varied by means of a frequency controller (18, 23, 35), and in that a phase comparator (17, DBM) for the phases of the output signals of the optoelectric transducers (PD12, PD13, PD22, PD23, PD32, PD33) is used to generate a control signal representing a phase difference, which control signal is fed to the frequency controller (18, 23, 35) to form a control loop for the interferometric phases ($\phi_2$, $\phi_3$).

7. The interferometer arrangement as claimed in claim 6, characterized in that the coherent radiation source (L1, L2) is designed to generate at least one reference beam ($v_1$) whose frequency corresponds approximately to the frequency of one of the measuring beams ($v_3$) and is harmonically coupled to the frequency of another measuring beam ($v_2$).

8. The interferometer arrangement as claimed in claim 6, characterized by a frequency multiplier assigned to a coherent radiation source (L1, L2).

9. The interferometer arrangement as claimed in claim 6, characterized in that use is made in a reference branch of the interferometer (13, 13') of a frequency modulator (30) whose controller is connected to a high frequency generator for two high frequencies ($\Omega$, $2\Omega$) whose frequency ratio to one another is that of the frequencies of the measuring beams ($v_2$, $v_3$).

* * * * *